United States Patent
Rees et al.

(10) Patent No.: US 6,699,825 B2
(45) Date of Patent: Mar. 2, 2004

(54) ACIDIC HARD-SURFACE ANTIMICROBIAL CLEANER

(75) Inventors: Wayne M. Rees, Caledonia, WI (US); Debra S. Hilgers, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 184 days.

(21) Appl. No.: 09/760,035

(22) Filed: Jan. 12, 2001

(65) Prior Publication Data

US 2002/0155969 A1 Oct. 24, 2002

(51) Int. Cl.$^7$ .............................. C11D 7/08; C11D 3/44
(52) U.S. Cl. ..................... 510/180; 510/181; 510/182; 510/243; 510/245; 510/253; 510/271; 510/362; 510/405; 510/426; 510/432
(58) Field of Search ................... 510/180, 182, 510/181, 243, 245, 253, 271, 362, 405, 426, 432

(56) References Cited

U.S. PATENT DOCUMENTS

| | | |
|---|---|---|
| 3,915,633 A | 10/1975 | Ramachandran ............... 8/137 |
| 3,969,258 A | 7/1976 | Carandang et al. .......... 252/106 |
| 4,690,779 A | 9/1987 | Baker et al. ................ 252/546 |
| 4,863,629 A | 9/1989 | Osberghaus et al. |
| 4,975,217 A | 12/1990 | Brown-Skrobot et al. .. 252/107 |
| 5,122,541 A | 6/1992 | Eggensperger et al. ..... 514/578 |
| 5,436,008 A | 7/1995 | Richter et al. .............. 424/405 |
| 5,750,482 A * | 5/1998 | Cummings ................. 510/182 |
| 5,891,392 A | 4/1999 | Monticello et al. |
| 5,925,606 A * | 7/1999 | Stamm ........................ 510/238 |
| 5,962,388 A * | 10/1999 | Sherry et al. ................ 510/238 |
| 6,096,701 A * | 8/2000 | Mondin et al. .............. 510/382 |
| 6,106,774 A * | 8/2000 | Monticello et al. ........... 422/28 |
| 6,121,224 A * | 9/2000 | Fonsny et al. .............. 510/384 |
| 6,159,925 A * | 12/2000 | Blandiaux ................... 510/437 |
| 6,221,823 B1 * | 4/2001 | Crisanti et al. .............. 510/238 |
| 6,262,003 B1 * | 7/2001 | Leonard et al. .............. 510/238 |
| 6,281,182 B1 * | 8/2001 | Leonard et al. .............. 510/235 |
| 6,346,508 B1 * | 2/2002 | Leonard et al. .............. 510/417 |

FOREIGN PATENT DOCUMENTS

| | | |
|---|---|---|
| DE | 3713998 | 11/1988 |
| EP | 1001012 | 5/2000 |
| WO | WO 97/15649 | 5/1997 |
| WO | WO 97/36980 | 10/1997 |
| WO | WO 98/31776 | 7/1998 |
| WO | WO 00/00026 | 1/2000 |
| WO | WO 01/57174 | 8/2001 |

\* cited by examiner

*Primary Examiner*—Charles Boyer

(57) ABSTRACT

A low residue antimicrobial solution containing about 0.2 percent by weight of an acid selected from the group consisting of organocarboxylic acids; and about 2 percent of a volatile solvent selected from the group consisting of n-butanol, benzyl alcohol, phenylethanol, and sparingly soluble glycol ether solvents is disclosed. Preferred compositions may also contain about 0.1 percent anionic sulfated or sulfonated surfactants and about 5 percent co-solvent selected from the group consisting of completely water soluble monoprotic aliphatic alcohols and glycol ethers. The solution may be also employed as a low-residue cleaner for soiled hard surfaces.

21 Claims, No Drawings

ACIDIC HARD-SURFACE ANTIMICROBIAL CLEANER

RELATED APPLICATION(S)

Not applicable.

FEDERALLY SPONSORED RESEARCH OR DEVELOPMENT

Not applicable

BACKGROUND OF THE INVENTION

1. Technical Field

This invention relates to aqueous liquid cleaning and antimicrobial compositions which leave a low residue of material on the surface to be cleaned. The compositions of the present invention contain a synergistic combination of specific amounts of certain organocarboxylic acids and sparingly water-soluble monohydric aliphatic alcohol solvents, such as benzyl alcohol and certain low molecular weight glycol ethers. Anionic sulfated or sulfonated surfactants and co-solvents are also included in the preferred compositions.

2. Background Art

Eliminating pathogenic micro-organisms on various surfaces, especially hard surfaces where such organisms may stay active for relatively long periods of time, continues to be a desire of consumers. Traditionally, quaternary ammonium compounds, high levels of certain alcohols, and oxidizing agents have been used in anti-microbial household cleaning products. Disadvantages of utilizing these types of agents include their tendency to cause eye and skin irritation, unpleasant odor, high levels of volatile organic compounds (VOC's), and potential surface damage effects. Some types of hard surfaces, notably glass, glazed ceramic, and polished metal present an additional problem for cleaning and disinfecting. The visible appearance of these surfaces after cleaning is negatively affected by residues left on the surface by the cleaning composition, even after wiping by the user. Rinsing the surface with fresh water after cleaning would help remove these unsightly residues, but this step adds additional work to the cleaning process. Thus, there exists a need for cleaning and disinfecting compositions which can be used on various hard surfaces, especially glass, glazed ceramic, and polished metals, without leaving unsightly residues. Additionally, it is advantageous that such compositions are comprised largely of water, avoiding the use of large amounts of alcohols such as ethanol or isopropanol for reasons of cost, safety, and minimization of formulation VOC's.

Certain acids are known to have antimicrobial properties and are recognized as antimicrobial agents by governmental agencies such as the United States Environmental Protection Agency. For example, using the National Pesticide Information Retrieval System (Center for Environmental and Regulatory Information Systems, Purdue University, West Lafayette, Ind.), one can search a database of current US EPA disinfectant registrations. Such a search will indicate that substances such as citric acid, hydrochloric acid, lactic acid, phosphoric acid, propionic acid, and sulfuric acid are EPA recognized antimicrobial actives.

Many current anti-bacterial acid compositions in food and industrial sanitizing applications tend to utilize dilutable concentrates, some of which employ strong acids such as hydrochloric, phosphoric, organophosphonic, sulfuric, or organosulfonic acids. However, the use of cleaning compositions containing strong acids, especially phosphorous-containing acids, is undesirable for the formulation of household cleaning products for consumer use. Weak organic acids are desirable, such as lactic acid and citric acid, and are recognized by the United States Environmental Protection Agency as antimicrobial actives. Because they are weak acids, they are generally safer to use than mineral acids, both for the user and the surfaces to which they are applied. However, these acids generally do not have strong antimicrobial properties when used by themselves at low levels in aqueous solutions. Ideally, a second agent must be employed in combination with low levels of such weak acids, such that this second agent enhances the antimicrobial activity of the composition and also does not contribute to unsightly residue left on the surface after cleaning.

It is also known that certain acid-anion surfactant combinations can be used to formulate anti-microbial cleaners and surface treatments. For example, acid-anionic sanitizers have been successfully used in various industrial antimicrobial applications, such as in the food processing equipment and dairy industries. Non-volatile surfactants are used in these formulations, and therefore will remain on the surface to some extent once applied, unless rinsed away with clean water. Optimum efficacy is usually obtained at a pH of 3 or less. To avoid corrosion problems, and to minimize safety concerns, a pH range of from about 2 to 3 is preferred, which also provides some cleaning efficacy against low to moderate levels of hard-water soiling or spotting.

The prior art includes many compositions for cleaning hard surfaces, some of which include acidic antibacterial, or antimicrobial, components. Among these, U.S. Pat. No. 3,969,258, of Carandang, et al, teaches low foaming acid sanitizer compositions containing anionic surfactants which normally exhibit high-foaming characteristics. A foam suppressant combination of a $C_8$ to $C_{18}$ aliphatic alcohol, or a $C_9$ to $C_{12}$ alkyl phenol, and a polyvalent metal salt is present, and additional solubilizing glycols and alcohol may also be present. The reference, however, indicates that a pH of below 3.5 is necessary to achieve the desired result, and while weaker acids such as citric acid may be used, a stronger acid is normally used in combination therewith to achieve the pH desired.

Ramachandran, in U.S. Pat. No. 3,915,633, teaches a pre-wash combination utilizing as its primary active ingredient an organic acid capable of complexing stain-forming metallic ions in soil on a fabric. The organic complexing acid is selected from citric acid, succinic acid, tartaric acid, maleic acid, fumaric acid, and mixtures thereof, in concentrations of from 1 to 20 percent.

Baker et al, in U.S. Pat. No. 4,690,779, teach a substantially non-streaking, hard surface aqueous cleaning composition comprising from about 0.05% to 25.0% surfactant; from about 0.05% to 25.0% of an unbranched straight chain polymer of molecular weight less than 5000; from about 0.05% to 25.0% of an aqueous solvent; from about 0.05% to 25% builder; and the remainder water. Thus, the cleaner of this reference comprises a surfactant, a polymer, a solvent, and a builder, in addition to water.

A liquid hard surface cleaner having disinfectancy, comprising pine oil and organic oil soluble acids at an acid pH, is taught by Spaulding, et al, in U.S. Pat. No. 4,867,898. The reference teaches the use of organic oil soluble acids such as benzene carboxylic acids or hydroxy carboxylic acids, in combination with the pine oil and optional detergent agents.

Brown-Skrobot, et al, in U.S. Pat. No. 4,975,217, teach germicidal compositions for direct application to human skin, including an organic acid and a surfactant as active agents, and optionally also use an alcohol. The composition is intended for use in lotions and sprays, as well as in cleansers.

Eggensperger, et al, in U.S. Pat. No. 5,122,541, teach an aqueous surface disinfectant composition comprising as essential components a mixture of ethyl alcohol and isopropyl alcohol, a mixture of anionic surfactants, and a pH modifying agent to provide a pH from about 2 to 6, or from about 8 to 12.

In U.S. Pat. No. 5,436,008, Richter et al. teach that a microbial composition comprising a major portion of carrier and an effective sanitizing amount of octanoic acid or octanoic acid derivatives, and a sulfur containing compound, may be used for dairy farms, food and beverage processing plants, kitchens, food serving establishments, and for general utility in domestic households.

In addition to the above, U.S. Pat. No. 5,750,482, of Cummings, teaches a non-streaking glass cleaning composition comprising an ethylene glycol monohexyl ether, a surfactant, an organic cosolvent comprising a mixture of a low boiling organic cosolvent and a high boiling organic cosolvent, a builder, and water, said composition effective in a pH range from about 3.5 to about 11.5 as a glass cleaning composition.

BRIEF SUMMARY OF THE INVENTION

To minimize expense and possible visible detrimental effects of antimicrobial compositions on surfaces to be treated, it is desirable to minimize the amount of antimicrobial agent left on a surface after cleaning, while still retaining efficacy against pathogenic micro-organisms, such as *Staphylococcus aureus* and *Klebsiella pneumoniae*. For acid-based biocidal chemistries to be used by consumers, it is also desirable to maintain an effectively acidic pH regime (about pH 4 or below), without being so strongly acidic as to present a hazard to the user. As will be explained in greater detail below, we have found that a combination of weakly acidic organocarboxylic acids and select volatile low molecular weight monohydric alcohol solvents provides a biocidal composition that is effective against a broad range of micro-organisms. In the preferred embodiment of this invention, low levels of anionic sulfated or sulfonated surfactant are also employed to improve the wetting and cleaning of soiled surfaces, and further enhance the biocidal properties of the composition. Co-solvents are also included in the preferred embodiment of this invention, to further improve the cleaning and evaporative properties of the invention. Such compositions were found to provide virtually no unsightly residues on cleaned surfaces, without the necessity of rinsing with fresh water after use.

Accordingly, an object of this invention is to provide a novel antimicrobial cleaning solution utilizing reduced concentrations of residual antimicrobial actives.

An additional object of this invention is to provide novel hard surface cleaning compositions that provide effective antimicrobial properties without leaving high levels of unsightly residue on the cleaning surface.

A third object of this invention is to provide novel hard surface cleaning compositions that provide effective acid-based antimicrobial chemistries in a pH regime which is generally regarded as safe for consumer household use.

A further object is to provide a method of reducing microbial pathogens from a surface while cleaning the surface without leaving highly visible deposits on the surface.

It has now been discovered that the use of low levels of select organocarboxylic acids and specific volatile monohydric alcohol solvents provides a cleaning composition with superior antimicrobial properties compared to formulations containing only similar levels of organocarboxylic acid. Preferred compositions also contain very low levels of anionic sulfated or sulfonated surfactants to improve formulation wetting and cleaning properties on soiled surfaces and to further enhance biocidal activity. Co-solvents are also included in the preferred embodiment of this invention, to further improve the cleaning and evaporative properties of the invention. Moreover, when these compositions are used as cleaners on hard surfaces, they leave virtually no unsightly residue upon wiping and drying.

This invention is directed to an antimicrobial cleaning composition comprising from about 0.01 to about 0.4 percent by weight of at least one organocarboxylic acid selected from those having an ionization constant of from about $1 \times 10^{-2}$ to about $1 \times 10^{-5}$ in water at 25° C., wherein the pH of the composition is from about 2 to about 4 at 25° C. In addition, the composition of the invention contains from about 0.25 percent to about 5 percent by weight of at least one sparingly water-soluble, volatile monohydric alcohol solvent selected from the group consisting of aliphatic alcohols or a glycol ether.

In a preferred mode, the inventive composition also contains from about 0.01 to about 0.3 percent by weight of at least one anionic sulfated or sulfonated surfactant selected from the group consisting of alkyl sulfates, alkyl sulfonates, and aryl sulfonates with alkyl or aryl substituents.

In another preferred mode of the invention, the composition also contains from about 0.5 to about 10 percent by weight of at least one low molecular weight monohydric alcohol co-solvent which is completely miscible with water at 25° C.

In yet another preferred mode of the invention, the composition contains from about 0.05 to 1 percent by weight of a 1,2-alkanediol, a 1,3-alkanediol, a 2,3-alkane diol, or a 2,4-alkane diol, such diols having a molecular weight of less than 200 atomic mass units.

Other objects, advantages, and features of the present invention shall be apparent to one of skill in the art after review of the specifications and claims.

DETAILED DESCRIPTION OF THE INVENTION

This invention is directed towards a low residue antimicrobial cleaning composition consisting of at least one organocarboxylic acid, comprising from about 0.01 to about 0.4 percent by weight of an aqueous solution. The organocarboxylic acid is selected from the group consisting having an ionization constant of from about $1 \times 10^{-2}$ to about $1 \times 10^{-5}$ in water at 25° C., wherein the pH of the composition is from about 2 to about 4 at 25° C. It is also believed that this pH range provides some cleaning efficacy against low to moderate levels of hard-water (mineral soil) stains.

Exemplary organocarboxylic acids include citric acid, lactic acid, glycolic acid, gluconic acid, glucoheptonic acid, malic acid, malonic acid, glutaric acid, succinic acid, adipic acid, formic acid, oxalic acid, acetic acid, propanoic acid, benzoic acid, phthalic acid, and mixtures thereof. Other suitable organocarboxylic acids include low molecular weight polymeric organocarboxylic acids (molecular weight average, $M_w$, below about 60,000 atomic mass units) such as poly(acrylic acid) and poly(maleic) acid homopolymers and copolymers. Examples include Goodrite K-7058® available from BF Goodrich Speciality Chemicals, and Belclene 901® available from FMC Corporation.

Preferably, the composition contains between from about 0.05 to 0.3 percent by weight of an acid selected from the group consisting of citric acid, lactic acid, glycolic acid, malic acid, acetic acid, propanoic acid, and polymeric acids with molecular weight averages from about 1000 to about 10,000 atomic mass units, and mixtures thereof.

The inventive composition also contains from about 0.25 percent to about 5 percent by weight of at least one sparingly water-soluble, volatile monohydric alcohol solvent selected from the group consisting of aliphatic alcohols or a glycol ether. The term "sparingly water soluble" is defined as having less than about 10 percent by weight solubility in water at 25° C. Exemplary solvents include n-butanol, benzyl alcohol, phenylethanol, and glycol ethers selected from the group consisting of:

(1) R—O—$CH_2CH_2$—OH, where R is n-pentyl, n-hexyl, phenyl, or benzyl;

(2) R'—O—($CH_2CH_2$—O)$_2$OH, where R' is n-hexyl, phenyl, or benzyl;

(3) R"—O—$CH_2CH$—($CH_3$)OH, where R" is n-butyl, n-pentyl, n-hexyl, phenyl, or benzyl; and (4) R"—O($CH_2CH$—($CH_3$)O)$_2$H, where R" is n-butyl, n-pentyl, n-hexyl, phenyl, or benzyl.

Thus, in accordance with the above, the preferred solvent is an ethylene or diethylene glycol ether wherein R comprises n-pentyl, n-hexyl, phenyl, or benzyl, and R' comprises n-hexyl, phenyl, or benzyl; or a propylene or dipropylene glycol ether wherein R" comprises n-butyl, n-pentyl, n-hexyl, phenyl, or benzyl. Preferably, the inventive composition contains from about 50 to about 95 percent by weight of the solvent required to achieve it's maximum solubility in water at 25° C.

A preferred mode of this invention is directed to an antimicrobial composition comprising from about 0.01 to about 0.3 percent by weight of at least one anionic surfactant selected from the group consisting of:

(i) linear $C_8$ to $C_{16}$ alkyl sulfates;

(ii) $C_8$ to $C_{16}$ alkyl sulfonates (iii) $C_8$ to $C_{16}$ alkyl benzenesulfonates;

(iV) $C_8$ to $C_{16}$ alkyl diphenyloxide disulfonates; and (v) $C_4$ to $C_{16}$ alkylated naphthalene sulfonates.

The anionic surfactant is preferably an alkyl sulfate such as sodium lauryl sulfate (hereinafter "SLS"), an alkyl benzene sulfonate such as sodium dodecyl benzene sulfonate (hereinafter "SDBS"), or mixtures thereof. Other preferred anionic surfactants include disodium dodecyldiphenyloxide disulfonates such as those sold under the tradename Dowfax 2A1® from The Dow Chemical Company, or sodium n-octylsulfonate such as Bioterge PAS-8® from the Stepan Company.

Most preferably, the anionic surfactant is selected from those utilizing an alkali metal or ammonium cation, due to their relatively low cost. The most preferable alkali metal is sodium because of the widespread commercial availability and low cost of the sodium salts of these anionic surfactants. The acid forms of the aryl sulfonate anionic surfactants may also be employed. Preferred examples include dodecylbenzene sulfonic acid and dodecyldiphenyloxide disulfonic acid, such as those sold under the tradename Biosoft®S-100 from the Stepan Company or Dowfax 2A0® from The Dow Chemical Company.

Completely water miscible monohydric volatile co-solvents are included in these aqueous solutions by the addition, for example, of ethyl or propyl alcohol or completely water soluble glycol ethers. These solvents are employed to enhance the cleaning and evaporative properties of the compositions. Exemplary volatile solvents include ethyl and propyl alcohols, and glycol ethers selected from the group consisting of the following formulae:

(a) R—O—$CH_2CH_2$—OH, where R is ethyl, propyl, or butyl (b) R'—O—($CH_2CH_2$—O)$_2$OH, where R' is ethyl, propyl, butyl, or pentyl (c) R"—O—$CH_2CH$—($CH_3$)OH, where R" is methyl, ethyl, or propyl (d) R'''—O—($CH_2CH$—($CH_3$)O)$_2$H, where R''' is methyl or ethyl Exemplary glycol ethers include diethylene glycol monoethyl ether, available under the tradename Carbitol® from Union Carbide Corp.; and dipropylene glycol methyl ether, available under the trade name Dowanol DPM® from The Dow Chemical Company. When employed, one or more co-solvents are typically present in a total amount ranging from about 0.5 to about 10 percent by weight; preferably about 1 to about 5 percent by weight of the solution.

The preferred mode of this invention may also contain low levels of a 1,2-alkanediol, a 1,3-alkanediol, a 2,3-alkanediol, or a 2,4-alkanediol, such diols having a molecular weight of less than 200 atomic mass units. Exemplary diols include 1,2-propanediol, 2-methyl-2,4-pentanediol, and 1,2-octanediol. When employed, the diols are typically present in an amount from about 0.05 to about 1 percent by weight; preferably about 0.1 to about 0.5 percent by weight of the solution. The inclusion of the above alkane-diols improves the cleaning and evaporative properties of the invention.

The inventive solution can be aqueous or non-aqueous. Aqueous solutions are most preferred. The aqueous solution of this invention will generally contain an amount of water in the range from about 85 to about 99 percent and preferably, from about 90 to about 98 percent by weight.

Other additives known in the cleaning and disinfecting arts may be included in the inventive solution. Such additives include, for example, wetting agents (i.e. fluorosurfactants), colorants, fragrances, preservatives and stabilizers.

Additionally, this invention is also directed to a method of cleaning with simultaneously reducing the microbial contamination present on a surface by the application of the composition to the substrate by wiping, mopping, spraying, misting, dripping, or the like. The method may comprise a single step of applying the solution onto the substrate without direct physical removal, or may comprise both application and removal steps such as spraying followed by wiping with a cloth. The method may also comprise the use of a cloth wipe substrate having been premoistened with the antimicrobial solution of the present invention.

Modes Of Carrying Out The Invention

The examples which follow are intended as an illustration of certain preferred embodiments of the invention. The amount of a component in a composition is expressed in percent by weight in an aqueous solution unless otherwise noted. In the examples which follow, various substances utilized are abbreviated as follows:

| | |
|---|---|
| LA | Lactic Acid |
| CA | Citric Acid |
| GA | Glycolic Acid |
| EGPE | Ethylene Glycol n-Pentyl Ether |
| DEGHE | Diethylene Glycol n-Hexyl Ether |
| EPh | Ethylene Glycol Phenyl Ether |
| BA | Benzyl Alcohol |
| Carbitol | Diethylene Glycol Ethyl Ether |
| DPM | Dipropylene Glycol Methyl Ether |
| IPA | Iso-propanol |

EXAMPLE 1

Aqueous Solubility Values For Select Solvents

Set forth in Table 1 are the solubility of various solvents suitable for use in the present invention, either as sparingly soluble solvents, or as completely soluble co-solvents.

TABLE 1

Aqueous solubility of select solvents

| Solvent | Solubility in water at 20–25° C. | Reference |
|---|---|---|
| EGPE | 3.4% | 1 |
| DEGHE | 1.4% | 2 |
| Eph | 2.3% | 3 |
| BA | 3.8% | 4 |
| Carbitol | Infinite | 2 |
| DPM | Infinite | 3 |
| IPA | Infinite | 4 |

References:
1. Union Carbide Corporation Product Safety Data Sheet-Pentyl Cellosolve
2. Union Carbide Corporation Glycol Ether Brochure
3. Dow Chemical Company Glycol Ethers Handbook
4. Merck Index, 11$^{th}$ Edition

EXAMPLE 2

Sanitizing Efficacy of Compositions Containing Organocarboxylic Acid and/or Sparingly Soluble Aliphatic Alcohols or Glycol Ethers Low-residue hard surface cleaner formulations of the present invention were evaluated for sanitizing efficacy under the United States Environmental Protection Agency's Non-Food Contact Sanitizer Test, DIS/TSS-10 (Jan. 7, 1982). As noted in specific examples, a 30 second or 1 minute contact time using a glass slide test surface was used. As these formulas are to be used as one-step antimicrobial cleaners, fetal bovine serum was added to the innoculum at a concentration of 5.0 percent by weight to simulate an organic soil load such as one would expect to find on a typical non-food contact surface prior to cleaning.

Efficacy of the test solutions was evaluated versus *Staphylococcus aureus* (*S. aureus*), *Klebsiella pneumoniae* (*K. pneumoniae*), and *Salmonella choleraesius* (*S. choleraesius*). As a control, parallel tests were conducted using a 0.01 percent solution of Triton X-100 (isooctylphenoxyl-polyethoxyethanol with 9–10 moles of oxyethylene) in an identical manner as the test solutions. The results for the test solutions were compared to the control and are reported as "Log Kill" of the test organism versus the control counts in Table 2. A "Log Kill" of 5 means that 99.999 percent of the organism has been killed.

TABLE 2

Acid & Acid-Solvent Combinations (1-minute contact times)

| Composition | Formula 1 | Organism | Log Kill |
|---|---|---|---|
| 0.10% LA | 2.8 | S. aureus | 2.8 |
| 0.10% CA | 2.7 | S. aureus | 3.0 |
| 0.10% GA | 2.8 | S. aureus | 2.9 |
| 1.5% EGPE | 7.0 | S. aureus | 3.3 |
| 1.0% DEGHE | 7.0 | S. aureus | 3.1 |
| 1.8% Eph | 7.0 | S. aureus | 3.9 |
| 1.5% BA | 7.0 | S. aureus | 2.8 |
| 2.0% Carbitol | 7.0 | S. aureus | 1.1 |
| 2.0% DPM | 7.0 | S. aureus | 1.6 |
| 2.0% IPA | 7.1 | S. aureus | 2.1 |
| 0.10% LA + 1.5% EGPE | 2.8 | S. aureus | ≧5.5 |
| 0.10% CA + 1.5% EGPE | 2.7 | S. aureus | ≧5.5 |
| 0.10% GA + 1.5% EGPE | 2.8 | S. aureus | ≧5.5 |
| 0.10% LA + 1.0% DEGHE | 2.8 | S. aureus | 4.7 |
| 0.10% CA + 1.0% DEGHE | 2.7 | S. aureus | 4.8 |
| 0.10% GA + 1.0% DEGHE | 2.8 | S. aureus | 5.2 |
| 0.10% CA + 1.8% EPh | 2.7 | S. aureus | 5.4 |
| 0.10% GA + 1.8% EPh | 2.8 | S. aureus | 5.1 |
| 0.10% CA + 1.5% BA | 2.7 | S. aureus | 5.4 |
| 0.10% GA + 1.5% BA | 2.8 | S. aureus | 5.1 |
| 0.10% LA + 2.0% DPM | 2.8 | S. aureus | 2.0 |
| 0.10% CA + 2.0% DPM | 2.7 | S. aureus | 2.6 |
| 0.10% LA + 2.0% IPA | 2.8 | S. aureus | 2.8 |
| 0.10% CA + 2.0% IPA | 2.7 | S. aureus | 2.2 |
| 0.10% LA + 2.0% Carbitol | 2.8 | S. aureus | 1.6 |
| 0.10% CA + 2.0% Carbitol | 2.7 | S. aureus | 1.3 |
| 0.10% LA | 2.8 | K. pneumoniae | 2.9 |
| 0.10% CA | 2.7 | K. pneumoniae | 2.5 |
| 0.10% GA | 2.8 | K. pneumoniae | 2.8 |
| 1.5% EGPE | 7.0 | K. pneumoniae | 4.7 |
| 1.0% DEGHE | 7.0 | K. pneumoniae | 4.3 |
| 1.8% Eph | 7.0 | K. pneumoniae | 4.2 |
| 1.5% BA | 7.0 | K. pneumoniae | 4.1 |
| 2.0% DPM | 7.0 | K. pneumoniae | 1.2 |
| 2.0% IPA | 7.0 | K. pneumoniae | 2.1 |
| 2.0% Carbitol | 7.0 | K. pneumoniae | 1.0 |
| 0.10% LA + 1.5% EGPE | 2.8 | K. pneumoniae | 4.9 |
| 0.10% CA + 1.5% EGPE | 2.7 | K. pneumoniae | ≧5.1 |
| 0.10% GA + 1.5% EGPE | 2.8 | K. pneumoniae | ≧5.1 |
| 0.10% LA + 1.0% DEGHE | 2.8 | K. pneumoniae | ≧5.1 |
| 0.10% CA + 1.0% DEGHE | 2.7 | K. pneumoniae | ≧5.1 |
| 0.10% LA + 1.8% EPh | 2.8 | K. pneumoniae | ≧5.1 |
| 0.10% CA + 1.8% EPh | 2.7 | K. pneumoniae | ≧5.1 |
| 0.10% LA + 1.5% BA | 2.8 | K. pneumoniae | ≧5.1 |
| 0.10% CA + 1.5% BA | 2.7 | K. pneumoniae | ≧5.1 |
| 0.10% CA + 2.0% DPM | 2.8 | K. pneumoniae | 2.7 |
| 0.10% LA + 2.0% DPM | 2.9 | K. pneumoniae | 2.3 |
| 0.10% CA + 2.0% IPA | 2.7 | K. pneumoniae | 2.0 |
| 0.10% LA + 2.0% IPA | 2.7 | K. pneumoniae | 2.1 |
| 0.10% CA + 2.0% Carbitol | 2.8 | K. pneumoniae | 0.8 |
| 0.10% LA + 2.0% Carbitol | 2.8 | K. pneumoniae | 1.1 |

It is necessary to demonstrate a bacterial reduction of at least 99.9 percent (≧ 3 log) over the parallel control count within 5 minutes in order to meet the efficacy requirements established by the US Environmental Protection Agency for a sanitizer. The data shown in Table 2 demonstrate that the formulations of the present invention are capable of achieving even a greater microbial reduction in significantly less time than is required to meet EPA standards (1 minute versus 5 minutes). As shown in Table 2, the combination of certain alcohol and glycol ether solvents with low levels of organocarboxylic acids produces a composition of considerable antimicrobial efficacy, as seen by the enhanced biocidal efficacy against *S. aureus* and *K. pneumoniae*. This is demonstrated for EGPE, DEGHE, EPh, and BA, all of which display limited solubility in water (soluble at less than 10 percent by weight in water at 25° C.). In contrast, carbitol, DPM and IPA are completely miscible in water and have no significant antimicrobial synergy with low levels of organocarboxylic acids, as shown for the results against *S.*

*aureus* and *K. pneumoniae* bacteria, when these solvents are used at dilute concentrations in an aqueous acidic solution.

EXAMPLE 3

Sanitizing Efficacy of Compositions Containing Organocarboxylic Acid, Sparingly Soluble Glycol Ether, Anionic Sulfonated Surfactant and Additional Alcohol and Glycol Ether Solvents It is necessary to demonstrate a bacterial reduction of at least 99.9 percent ($\geq$ 3 log) over the parallel control count within 5 minutes in order to meet the efficacy requirements established by the United States Environmental Protection Agency for a sanitizer.

TABLE 3A

Test Compositions

| Reagent | Formula 1 | Formula 2 |
|---|---|---|
| Lactic acid | 0.17% | 0.17% |
| Sodium dodecylbenzenesulfonate | 0.090% | 0.090% |
| Ethylene glycol n-hexyl ether | 0.60% | 0.60% |
| Diethylene glycol ethyl ether | 1.0% | 1.0% |
| Iso-propanol | 3.5% | 3.5% |
| Hexylene glycol | 0.25% | 0.25% |
| 3M Fluorad ®FC-120 Fluorosurfactant | 0.005% | -0- |

TABLE 3B

Sanitizer test results - 30 second contact times

| Composition | Test | Organism | Log Kill vs. Control |
|---|---|---|---|
| Table 3A, Formula 1 | 1 | S. aureus | $\geq$5 log reduction |
| Table 3A, Formula 1 | 1 | K. pneumoniae | $\geq$5 log reduction |
| Table 3A, Formula 1 | 2 | S. aureus | $\geq$5 log reduction |
| Table 3A, Formula 1 | 2 | K. pneumoniae | $\geq$5 log reduction |
| Table 3A, Formula 1 | 2 | S. choleraesius | $\geq$5 log reduction |
| Table 3A, Formula 2 | 1 | S. aureus | $\geq$5 log reduction |

The data shown in Table 3B demonstrates that the formulations of the present invention are capable of achieving even a greater microbial reduction in significantly less time than is required to meet EPA standards (30 seconds versus 5 minutes).

EXAMPLE 4

Evaluation of Disinfectant Efficacy of Compositions Containing Organocarboxylic Acid, Sparingly Soluble Glycol Ether, Anionic Sulfonated Surfactant, and Additional Alcohol and Glycol Ether Solvents Formulations were evaluated for disinfecting efficacy via the standard AOAC Germicidal Disinfectant Spray Test protocol using *Staphylococcus aureus, Klebsiella pneumoniae*, and *Salmonella choleraesius* as the test organisms. A 30-second contact time using a glass slide test surface was employed. The 5.0 percent fetal bovine serum was added to the innoculum as the formulas are intended for use as one-step disinfectant cleaners. Disinfectant results are listed as the number of failures (indicating positive microbial presence and growth) observed for number of carriers (referred to as replicates) evaluated for each formulation.

TABLE 4A

Test Compositions

| Reagent | Formula 1 | Formula 2 |
|---|---|---|
| Lactic acid | 0.17% | 0.17% |
| Sodium dodecylbenzenesulfonate | 0.090% | 0.090% |
| Ethylene glycol n-hexyl ether | 0.60% | 0.60% |
| Diethylene glycol ethyl ether | 1.0% | 1.0% |
| Iso-propanol | 3.5% | 3.5% |
| Hexylene glycol | 0.25% | 0.25% |
| 3M Fluorad ®FC-120 Fluorosurfactant | 0.005% | -0- |

TABLE 4B

Disinfectant Test Results-30 second contact time

| Composition | Test | Replicates | Organism | Failures |
|---|---|---|---|---|
| Table 4A, Formula 1 | 1 | 20 | S. aureus | 0 |
| Table 4A, Formula 1 | 1 | 20 | K. pneumoniae | 0 |
| Table 4A, Formula 1 | 2 | 30 | S. aureus | 0 |
| Table 4A, Formula 1 | 2 | 30 | K. pneumoniae | 0 |
| Table 4A, Formula 1 | 2 | 30 | S. choleraesius | 0 |
| Table 4A, Formula 2 | 3 | 40 | S. aureus | 0 |

The data shown in Table 4B demonstrates that the formulations of the present invention are capable of achieving disinfection performance, as measured by the standard AOAC Germicidal Disinfectant Spray Test, in a significantly shorter contact time than is required to meet United States EPA standards (30 seconds versus 10 minutes).

EXAMPLE 5

Evaluation of Visible Surface Residue (No Rinsing or Wiping)

Test formulations were sprayed onto various surfaces and allowed to drain, without wiping or rinsing. The surfaces were then rated for the appearance of visible residue. Surfaces employed as coupons were:

Clear glass plates (5×7 inches)
Glazed black ceramic tiles (4×4 inches)
Chromed steel (5×4.5 inches)

All coupons were pre-cleaned with Alconox® Powdered Precision Cleaner, followed by thorough rinsing with tap water, and a final rinsing with deionized water. The coupons were allowed to drain and air dry in racks, inclined at 70–80° from a horizontal position, and air dried at room temperature and ambient humidity for at least 24 hours prior to use in the treatment and evaluation procedure.

Coupons were inclined at 70–80° from a horizontal position, and the surface thoroughly covered with liquid cleaner treatment by spraying from a trigger sprayer equipped bottle. The wet treated coupons were allowed to drain and air dry in racks, inclined at 70–80° from a horizontal position at room temperature and ambient humidity for approximately 16–20 hours prior to visual evaluation of the surface for residues. Commercial products were used in their containers as sold. The glass coupons were treated on both sides of the coupon, while the black ceramic tiles and chromed steel coupons were treated only on the side having a black/chromed surface. The employed treatment solutions were as follows:

Comet ® Homecare Bathroom Heavy Duty Cleaner with Disinfectant
Formula 409® All Purpose Cleaner Lysol® Disinfectant Basin Tub and Tile Cleaner
Windex® Antibacterial Glass & Surface Cleaner
Inventive Formula, Example 5
Deionized water

TABLE 5A

Inventive Formula, Example 5

| Reagent | Weight % |
|---|---|
| Lactic acid | 0.17% |
| Sodium dodecylbenzenesulfonate | 0.080% |
| Ethylene glycol n-hexyl ether | 0.78% |
| Diethylene glycol ethyl ether | 1.3% |
| Iso-propanol | 3.5% |
| Hexylene glycol | 0.325% |

Evaluation Procedure and Results:

Treated coupons were coded without any indication as to the identity of the treatment solution. Five panelists evaluated the treated coupons for the appearance of visible residue, using a 0 to 5 scale (0.5 increments), where 0=no visible residue, and 5=heavy visible residue.

TABLE 5B

Visible residue test results

TREATMENT COMPOSITION

| Coupon | Lysol | 409 | Water | Windex | Comet | Example 5 |
|---|---|---|---|---|---|---|
| Glass | | | | | | |
| Average | 5.0 | 4.0 | 0.9 | 3.6 | 2.9 | 0.4 |
| Std Dev. | 0.0 | 0.4 | 0.5 | 1.0 | 0.4 | 0.4 |
| Black Tile | | | | | | |
| Average | 4.8 | 3.9 | 0.1 | 1.6 | 4.3 | 0.2 |
| Std Dev. | 0.4 | 0.5 | 0.2 | 1.5 | 0.6 | 0.3 |
| Chrome | | | | | | |
| Average | 4.3 | 3.6 | 0.6 | 4.3 | 4.2 | 0.4 |
| Std Dev. | 0.3 | 1.2 | 0.4 | 0.4 | 1.1 | 0.2 |

Conclusions:

The inventive formula, example 5,0 leaves essentially no visible residue on glass, ceramic or chrome surfaces, being equivalent to deionized water in appearance, and outperforms all the commercially available disinfectants/sanitizers tested.

EXAMPLE 6

Antimicrobial Wipes Pre-Moistened With Inventive Solution

TABLE 6

Liquid Antimicrobial Composition

| Reagent | Formula 6 |
|---|---|
| Lactic acid | 0.21% |
| Dodecylbenzene sulfonic acid | 0.080% |
| Ethylene glycol n-hexyl ether | 0.85% |
| Diethylene glycol n-butyl ether | 0.75% |
| Iso-propanol | 3.5% |
| Hexylene glycol | 0.30% |

The inventive solution is evenly applied to a Dexter Hydraspun® 10234 non-woven substrate (Dexter Corporation, Windsor Locks, Conn., USA) at a liquid loading of 250% by weight (liquid to cloth substrate). The resulting moistened cloth is useful for cleaning a variety of hard surfaces, where antimicrobial and low residue properties are desired. Such cloth substrates may comprise paper, woven fabrics, and non-woven fabrics, of such commonly employed materials as cotton, nylon, polyester, cellulose, and other conventional fibrous materials used in the preparation of wiping cloths. Such cloths may be provided with a liquid loading of from about 100 to 500 percent by weight of liquid cleaner per unit weight of cloth.

INDUSTRIAL APPLICABILITY

The compositions of this invention are highly effective for reducing pathogenic microbes and cleaning the multiple surfaces typically found in bathroom and kitchen areas, such as glass, ceramic tiles, chrome, stainless steel, Formica, and other similar surfaces where visible residue is critical to appearance. The composition can be prepared by conventional manufacturing processes and equipment and dispensed in packaging typically utilized for liquid cleaners. The compositions can also be used to prepare moistened cloth wipes having substantial antimicrobial properties. Other variations and modifications of this invention will be obvious to those skilled in the art.

What is claimed is:

1. A low residue antimicrobial aqueous cleaning composition in the form of a sanitizing solution, comprising:

from about 0.01 to about 0.4 weight percent of at least one organocarboxylic acid having an ionization constant of from about $1 \times 10^{-2}$ to about $1 \times 10^{-5}$ in water at 25° C., wherein the acid is selected from the group consisting of lactic acid and glycolic acid;

wherein the pH of the composition is from about 2 to about 4 at 25° C., and said composition further comprises less than 0.3% by weight of anionic surfactant if anionic surfactant is present, and from about 0.25 to about 5 weight percent of a sparingly soluble monohydric solvent selected from the group consisting of n-butanol, benzyl alcohol, phenylethanol, R—O—CH$_2$CH$_2$—OH, where R is n-pentyl, n-hexyl, phenyl, or benzyl; R'—O—(CH$_2$CH$_2$—O)$_2$OH, where R' is n-hexyl, phenyl, or benzyl; R"—O—CH$_2$CH—(CH$_3$)OH, where R" is n-butyl, n-pentyl, n-hexyl, phenyl, or benzyl; and R'"—O—(CH$_2$CH—(CH$_3$)O)$_2$H, where R'" is n-butyl, n-pentyl, n-hexyl, phenyl, or benzyl, said solvent having less than about 10 percent by weight solubility in water at 25° C., wherein an oxidizing agent is not used in the cleaning composition, and wherein a quaternary ammonium compound is not used in the cleaning composition.

2. The composition of claim 1, wherein there is from 0.01 to 0.4 weight percent of the organocarboxylic acid, and that acid has an ionization constant of from $1 \times 10^{-2}$ to $1 \times 10^{-5}$ in water at 25° C.; and wherein the pH of the composition is from 2 to 4 at 25° C., and there is in the composition from 0.25 to 5 weight percent of the sparingly soluble monohydric solvent.

3. The composition of claim 1, further comprising from about 0.01 to about 0.3 percent by weight of an anionic surfactant selected from the group consisting of linear C$_8$ to C$_{16}$ alkyl sulfates, C$_8$ to C$_{16}$ alkyl sulfonates, C$_8$ to C$_{16}$ alkyl benzene sulfonates, C$_8$ to C$_{16}$ alkyl diphenyloxide disulfonates, and C$_4$ to C$_{16}$ alkylated naphthalene sulfonates, and mixtures thereof.

4. The composition of claim 3, wherein the surfactant is selected from the group consisting of sodium lauryl sulfate, sodium dodecylbenzene sulfonate, disodium dodecyldiphenyloxide disulphonate, dodecylbenzene sulfonic acid, and dodecyldiphenyloxide disulfonic acid, and mixtures thereof.

5. The composition of claim 1, further comprising from about 0.5 to about 10 percent by weight of a co-solvent selected from the group consisting of ethyl alcohol, propyl alcohol, and completely water soluble glycol ethers.

6. The composition of claim 5, wherein said co-solvent is a glycol ether selected from the group consisting of R—O—$CH_2$—$CH_2$—OH, where R is ethyl, propyl or butyl, R'—O—$(CH_2CH_2)_2$OH, where R' is ethyl, propyl, butyl, or pentyl, R''—O—$CH_2CH$—$(CH_3)$OH, where R'' is methyl, ethyl, or propyl, and R'''—O—$(CH_2CH$—$(CH_3)O)_2$H, where R''' is methyl or ethyl.

7. The composition of claim 5, wherein said co-solvent is selected from the group consisting of ethylene glycol n-butyl ether, diethylene glycol mono-ethyl ether, diethylene glycol mono-butyl ether, diethylene glycol mono-pentyl ether, propylene glycol mono-propyl ether, dipropylene glycol mono-methyl ether, and dipropylene glycol mono-ethyl ether.

8. A low residue antimicrobial aqueous cleaning composition, comprising:

from about 0.01 to about 0.4 weight percent of at least one organocarboxylic acid having an ionization constant of between about $1 \times 10^{-2}$ to about $1 \times 10^{-5}$ in water at 25° C.;

from about 0.25 to about 5 weight percent of a sparingly soluble monohydric solvent selected from the group consisting of aliphatic alcohols and glycol ethers, said solvent having less than about 10 percent by weight solubility in water at 25° C.; and from about 0.05 to about 1 percent by weight of an alkanediol having a molecular weight of less than 200 atomic mass units, selected from the group consisting of 1,2-alkanediols, 1,3-alkanediols, 2,3-alkanediols, and 2,4-alkanediols;

wherein said at least one organocarboxylic acid is selected from the group consisting of citric acid, lactic acid, glycolic acid, malic acid, acetic acid, propanoic acid, and mixtures thereof, and said monohydric solvent is a glycol ether selected from the group consisting of R—O—$CH_2CH_2$—OH, where R is n-pentyl, n-hexyl, phenyl, or benzyl; R'—O—$(CH_2CH_2$—O$)_2$OH, where R'' is n-hexyl, phenyl, or benzyl; R''—O—$CH_2CH$—$(CH_3)$OH, where R'' is n-butyl, n-pentyl, n-hexyl, phenyl, or benzyl; and R'''—O—$(CH_2CH$—$(CH_3)O)_2$H, where R''' is n-butyl, n-pentyl, n-hexyl, phenyl, or benzyl: and wherein the pH of the composition is from about 2 to about 4 at 25° C.

9. The composition of claim 1, further comprising from about 0.01 to about 0.3 percent by weight of an anionic surfactant selected from the group consisting of sodium lauryl sulfate, sodium dodecylbenzene sulfonate, disodium dodecyldiphenyloxide disulphonate, dodecylbenzene sulfonic acid, and dodecyldiphenyloxide disulfonic acid, and mixtures thereof; from about 1 to about 5 percent by weight of a co-solvent selected from the group consisting of ethyl alcohol, propyl alcohol, and completely water soluble glycol ethers, and from about 0.1 to bout 0.5 percent by weight of an alkanediol having a molecular weight of less than 200 atomic mass units.

10. The composition of claim 9, wherein said co-solvent is selected from the group consisting of ethylene glycol n-butyl ether, diethylene glycol mono-ethyl ether, diethylene glycol mono-butyl ether, diethylene glycol mono-pentyl ether, propylene glycol mono-propyl ether, dipropylene glycol mono-methyl ether, and dipropylene glycol mono-ethyl ether.

11. A method of sanitizing a hard surface comprising:

exposing the surface to an aqueous cleaning composition comprising from about 0.05 to about 0.3 weight percent of at least one organocarboxylic acid having an ionization constant of from about $1 \times 10^{-2}$ to about $1 \times 10^{-5}$ in water at 25° C., wherein the acid is selected from the group consisting of lactic acid and glycolic acid, wherein the pH of the composition is from about 2 to about 4 at 25° C., and said composition further comprises less than 0.3% by weight of anionic surfactant if anionic surfactant is present, and from about 0.25 to about 5 weight percent of a sparingly soluble monohydric solvent selected from the group consisting of n-butanol, benzyl alcohol, phenylethanol, and glycol ethers, wherein said glycol ethers are selected from the group consisting of R—O—$CH_2CH_2$—OH, where R is n-pentyl, n-hexyl, phenyl, or benzyl; R'—O—$CH_2CH_2$—O$)_2$OH, where R' is n-hexyl, phenyl, or benzyl; R''—O—$CH_2CH$—$(CH_3)$OH, where R'' is n-butyl, n-pentyl, n-hexyl, phenyl, or benzyl; and R'''—O—$(CH_2CH$—$(CH_3)O)_2$H, where R''' is n-butyl, n-pentyl, n-hexyl, phenyl, or benzyl, said solvent having less than about 10 percent by weight solubility in water at 25° C., and wherein an oxidizing agent is not used in the cleaning composition, and wherein a quaternary ammonium compound is not used in the cleaning composition;

then allowing the surface to dry;

the method not including a rinsing step between the exposing step and the drying step;

whereby the surface is sanitized.

12. The method of claim 11, wherein said composition further comprises from about 0.01 to about 0.3 percent by weight of an anionic surfactant selected from the group consisting of linear $C_8$ to $C_{16}$ alkyl sulfates, $C_0$ to $C_{14}$ alkyl sulfonates, $C_8$ to $C_{16}$ alkyl benzene sulfonates, $C_8$ to $C_{16}$ alkyl diphenyloxide disulfonates, and $C_4$ to $C_{16}$ alkylated naphthalene sulfonates, and mixtures thereof.

13. The method of claim 12, wherein the surfactant is selected from the group consisting of sodium lauryl sulfate, sodium dodecylbenzene sulfonate, disodium dodecyldiphenyloxide disulphonate, dodecylbenzene sulfonic acid, and dodecyldiphenyloxide disulfonic acid, and mixtures thereof.

14. The method of claim 11, wherein the composition further comprises from about 0.5 to about 10 percent by weight of a co-solvent selected from the group consisting of ethyl alcohol, propyl alcohol, and completely water soluble glycol ethers.

15. The method of claim 14, wherein said co-solvent is a glycol ether selected from the group consisting of R—O—$CH_2CH_2$—OH, where R is ethyl, propyl, or butyl; R'—O—$(CH_2CH_2$—O$)_2$OH, where R' is ethyl, propyl, butyl, or pentyl; R''—O—$CH_2CH$—$(CH_3)$OH, where R'' is methyl, ethyl, or propyl; and R'''—O—$(CH_2CH$—$(CH_3)O)_2$H, where R''' is methyl or ethyl.

16. An aqueous cleaning solution, comprising:

from about 0.05 to about 0.2 weight percent of at least one organocarboxylic acid having an ionization constant of from about $1 \times 10^{-2}$ to about $1 \times 10^{-5}$ in water at 25° C.;

wherein said at least one organocarboxylic acid is selected from the group consisting of citric acid, lactic acid, glycolic acid, malic acid, acetic acid, propanoic acid, and mixtures thereof, and said monohydric solvent is a glycol ether selected from the group consisting of R—O—CH$_2$CH$_2$—OH, R'—O—(CH$_2$CH$_2$O)$_2$OH, R"—O—CH$_2$CH—(CH$_3$)OH, and R'"—O(CH$_2$CH—(CH$_3$)O)$_2$H, wherein R is n-pentyl, n-hexyl, phenyl, or benzyl, R' is n-hexyl, phenyl, or benzyl, and R" is n-butyl, n-pentyl, n-hexyl, phenyl, or benzyl;

from about 0.25 to about 5 weight percent of a sparingly soluble monohydric solvent selected from the group consisting of n-butanol, benzyl alcohol, phenylethanol, and glycol ethers, said solvent having less than about 10 percent by weight solubility in water at 25° C.; and from about 0.05 to about 1 percent by weight of an alkanediol having a molecular weight of less than 200 atomic mass units, selected from the group consisting of 1,2-alkanediols, 1,3-alkanediols, 2,3-alkanediols; and 2,4-alkanediols;

wherein the pH of the composition is from about 2 to about 4 at 25° C.

17. The method of claim 11, wherein the composition further comprises:

from about 0.01 to about 0.3 percent by weight of an anionic surfactant selected from the group consisting of sodium lauryl sulfate, sodium dodecylbenzene sulfonate, disodium dodecyldiphenyloxide disulphonate, dodecylbenzene sulfonic acid, and dodecyldiphenyloxide disulfonic acid, and mixtures thereof; and from about 1 to about 5 percent by weight of a co-solvent selected from the group consisting of ethyl alcohol propyl alcohol, and completely water soluble glycol ethers; and up to about 0.5 percent by weight of an alkanediol having a molecular weight of less than 200 atomic mass units, selected from the group consisting of 1,2-alkanediols, 1,3-alkanediols, 2,3-alkanediols, and 2,4-alkanediols, 1,3-alkanediols, 2,3-alkanediols, and 2,4-alkanediols.

18. The method of claim 11, wherein the composition has 0.05 to 0.3 weight percent of an organocarboxylic acid having an ionization constant of from $1\times10^{-2}$ to $1\times10^{-5}$ in water at 25° C.; and wherein the pH of the composition is from 2 to 4 at 25° C. and there is from 0.25 to 5 weight percent of the sparingly soluble monohydric solvent where that solvent has less than 10 percent by weight solubility in water at 25° C.

19. An aqueous solution, comprising:
from 0.17 to 0.21 weight percent lactic acid;
from 0.60 to 0.85 weight percent of ethylene glycol n-hexyl ether;
from 0.75 to 1.30 weight percent diethylene glycol ethyl ether;
from 0.08 to 0.09 weight percent sodium dodecylbenzenesulfonate;
less than 5 weight percent isopropanol, and in any event about 3.5 weight percent isopropanol; and
from 0.25 to 0.325 weight percent hexylene glycol;
said solution having a pH of from 2 to 4 at 25° C.

20. A premoistened wipe comprising a fabric moistened with a liquid cleaning composition, the liquid cleaning composition comprising:
from 0.17 to 0.21 weight percent lactic acid;
from 0.60 to 0.78 weight percent of ethylene glycol n-hexyl ether;
from 0.75 to 1.30 weight percent diethylene glycol ethyl ether;
from 0.08 to 0.09 weight percent sodium dodecylbenzenesulfonate;
less than 5 weight percent isopropanol, and in any event about 3.5 weight percent isopropanol;
from 0.25 to 0.325 weight percent hexylene glycol; and
from 0.05 to 1 percent by weight of an alkanediol having a molecular weight of less than 200 atomic mass units;
said composition having a pH of from 2 to 4 at 25° C.

21. A premoistened wiping cloth, comprising
a fabric substrate impregnated with a liquid loading of from 100 to 500 percent by weight of liquid cleaner per unit weight of cloth, said cleaner comprising an aqueous solution comprising:
about 0.21 weight percent lactic acid;
about 0.85 weight percent ethylene glycol n-hexyl ether;
about 0.75 weight percent diethylene glycol n-butyl ether;
about 3.5 weight percent isopropanol;
about 0.30 weight percent hexylene glycol;
about 0.08 weight percent dodecylbenzene sulfonic acid; and
the balance water;
wherein the pH of the composition is from 2 to 4 at 25° C.

* * * * *

UNITED STATES PATENT AND TRADEMARK OFFICE
CERTIFICATE OF CORRECTION

PATENT NO.    : 6,699,825 B2
DATED         : March 2, 2004
INVENTOR(S)   : Wayne M. Rees and Debra S. Hilgers It is certified that error appears in the above-identified patent and that said Letters Patent is hereby corrected as shown below:

Column 12,
Line 43, replace "R'—0—(CH$_2$CH$_2$.0)$_2$—OH" with -- R'—0—(CH$_2$CH$_2$—0)$_2$H --

Column 13,
Line 13, replace "R'—0—(CH$_2$CH$_2$)$_2$OH" with -- R'—O—(CH$_2$CH$_2$—0)$_2$H --
Line 46, replace "R'—0—(CH$_2$CH$_2$—0)$_2$OH" with -- R'—0—(CH$_2$CH$_2$—0)$_2$H --
Line 47, replace "R''" with -- R' --
Line 63, replace "bout" with -- about --

Column 14,
Lines 22-23, replace "R'—0—CH$_2$CH$_2$—0)$_2$OH" with -- R'—0—(CH$_2$CH$_2$—0)$_2$H --
Lines 56-57, replace "R'—0—(CH$_2$CH$_2$—0)$_2$OH" with -- R'—0—(CH$_2$CH$_2$—0)$_2$H --

Column 15,
Line 4, replace "R'—0—(CH$_2$CH$_2$0)$_2$OH" with -- R'—0—(CH$_2$CH$_2$—0)$_2$H --
Line 18, after "2.3-alkanediols" replace ";" with -- , --
Line 40, delete extra line ", 1,3-alkanediols, 2,3-alkanediols, and 2,4-alkanediols."

Signed and Sealed this

Third Day of May, 2005

JON W. DUDAS
*Director of the United States Patent and Trademark Office*